(12) United States Patent
Van Valen (10) Patent No.: US 10,039,932 B2
(45) Date of Patent: Aug. 7, 2018

(54) EYELID TREATMENT DEVICE

(71) Applicant: Biolase, Inc., Irvine, CA (US)

(72) Inventor: Marcia Van Valen, Aliso Viejo, CA (US)

(73) Assignee: BIOLASE, INC., Irvine, CA (US)

( * ) Notice: Subject to any disclaimer, the term of this patent is extended or adjusted under 35 U.S.C. 154(b) by 89 days.

(21) Appl. No.: 13/837,983

(22) Filed: Mar. 15, 2013

(65) Prior Publication Data

US 2014/0142663 A1 May 22, 2014

Related U.S. Application Data

(60) Provisional application No. 61/728,576, filed on Nov. 20, 2012.

(51) Int. Cl.
| A61B 18/20 | (2006.01) |
| A61B 18/22 | (2006.01) |
| A61N 5/06 | (2006.01) |
| A61N 5/067 | (2006.01) |

(52) U.S. Cl.
CPC ...... *A61N 5/0616* (2013.01); *A61N 2005/063* (2013.01); *A61N 2005/067* (2013.01); *A61N 2005/0644* (2013.01)

(58) Field of Classification Search
None
See application file for complete search history.

(56) References Cited

U.S. PATENT DOCUMENTS

| 2,186,143 A | * | 1/1940 | Neugass | 600/212 |
| 2,247,258 A | * | 6/1941 | Shepard | A61B 1/24 |
| | | | | 116/DIG. 26 |
| 3,592,199 A | * | 7/1971 | Ostensen | 600/198 |
| 3,638,644 A | * | 2/1972 | Reick | A61B 1/267 |
| | | | | 600/191 |
| 3,641,332 A | * | 2/1972 | Reick et al. | 362/582 |
| 4,156,424 A | * | 5/1979 | Burgin | A61B 1/32 |
| | | | | 600/212 |
| 4,344,419 A | * | 8/1982 | Burgin | A61B 1/24 |
| | | | | 600/212 |
| 4,807,599 A | * | 2/1989 | Robinson | A61B 1/07 |
| | | | | 433/29 |
| 4,996,976 A | * | 3/1991 | Nakagawa | A61B 1/07 |
| | | | | 362/572 |

(Continued)

FOREIGN PATENT DOCUMENTS

| WO | WO 2013003594 A2 * | 1/2013 |
| WO | WO 2014018640 A1 * | 1/2014 |

OTHER PUBLICATIONS

International Search Report and Written Opinion dated Mar. 27, 2014 for corresponding PCT application No. PCT/US2013/066588.

(Continued)

*Primary Examiner* — Lynsey Eiseman
*Assistant Examiner* — Manolis Pahakis
(74) *Attorney, Agent, or Firm* — Greenberg Traurig LLP (57) ABSTRACT

A handpiece tip includes an optical waveguide with a proximal input end for receiving electromagnetic energy and a distal output end for emitting electromagnetic energy. The tip has an eyeball engagement surface with a concave contour, and has an oppositely facing eyelid engagement surface with a convex contour. The distal output end of the waveguide is located at the eyelid engagement surface.

12 Claims, 9 Drawing Sheets

(56) References Cited

U.S. PATENT DOCUMENTS

| | | | | |
|---|---|---|---|---|
| 5,047,008 | A | * | 9/1991 | de Juan, Jr. .......... A61F 9/00763 600/564 |
| 5,139,495 | A | * | 8/1992 | Daikuzono ............ A61B 18/22 606/17 |
| 5,190,535 | A | * | 3/1993 | Daikuzono ............ A61B 18/22 606/13 |
| 5,318,009 | A | * | 6/1994 | Robinson ................ A61B 1/24 362/120 |
| 5,328,488 | A | * | 7/1994 | Daikuzono ..................... 606/16 |
| 5,342,358 | A | * | 8/1994 | Daikuzono ............ A61B 18/28 606/15 |
| 5,372,595 | A | | 12/1994 | Gaasterland et al. |
| 5,451,221 | A | * | 9/1995 | Cho et al. ........................ 606/3 |
| 5,599,341 | A | * | 2/1997 | Mathis .................... A61F 9/008 606/5 |
| 6,029,304 | A | | 2/2000 | Hulke et al. |
| 6,120,518 | A | * | 9/2000 | Mark .................... A61B 90/36 606/170 |
| 6,129,721 | A | * | 10/2000 | Kataoka et al. .................. 606/2 |
| 6,139,489 | A | * | 10/2000 | Wampler ............ A61B 1/0008 600/109 |
| 6,176,824 | B1 | * | 1/2001 | Davis ...................... A61B 1/24 600/178 |
| 6,304,712 | B1 | * | 10/2001 | Davis ........................... 385/147 |
| 6,309,400 | B2 | * | 10/2001 | Beaupre ......... A61B 17/320068 606/169 |
| 6,319,240 | B1 | | 11/2001 | Beck |
| 6,319,274 | B1 | * | 11/2001 | Shadduck ....................... 607/89 |
| 6,432,046 | B1 | * | 8/2002 | Yarush .............. A61B 1/00039 600/109 |
| 6,516,216 | B1 | * | 2/2003 | Fontenot et al. ............. 600/473 |
| 7,141,048 | B1 | * | 11/2006 | Charles ........................... 606/4 |
| 7,384,419 | B2 | * | 6/2008 | Jones et al. ..................... 606/16 |
| 7,421,186 | B2 | * | 9/2008 | Boutoussov et al. ......... 385/146 |
| 7,563,222 | B2 | * | 7/2009 | Larsen et al. ..................... 600/3 |
| 7,891,146 | B1 | | 7/2011 | Korb et al. |
| 8,083,787 | B2 | | 12/2011 | Korb et al. |
| 8,128,674 | B2 | | 3/2012 | Korb et al. |
| 8,187,311 | B2 | | 5/2012 | Korb et al. |
| 8,255,039 | B2 | | 8/2012 | Gravely et al. |
| 8,320,725 | B2 | | 11/2012 | Temelkuran et al. |
| 8,790,366 | B2 | * | 7/2014 | Cordova ....................... 606/214 |
| 8,945,103 | B2 | * | 2/2015 | Chew et al. ...................... 606/6 |
| 2002/0009275 | A1 | * | 1/2002 | Williams ............ G02B 6/0008 385/123 |
| 2005/0182301 | A1 | * | 8/2005 | Acker .................... A61B 17/02 600/204 |
| 2006/0256575 | A1 | | 11/2006 | Vayser |
| 2006/0293645 | A1 | * | 12/2006 | Hibner .............................. 606/13 |
| 2007/0208226 | A1 | * | 9/2007 | Grey ...................... A61B 17/02 600/212 |
| 2008/0002426 | A1 | * | 1/2008 | Vayser ................. A61B 1/0623 362/574 |
| 2008/0021370 | A1 | * | 1/2008 | Bornstein ................. A61L 2/08 604/20 |
| 2008/0081999 | A1 | | 4/2008 | Gravely et al. |
| 2008/0195128 | A1 | * | 8/2008 | Orbay ................ A61B 1/00048 606/170 |
| 2008/0200758 | A1 | * | 8/2008 | Orbay ................ A61B 1/00048 600/112 |
| 2009/0054853 | A1 | * | 2/2009 | Huyser .................. A61B 17/02 604/264 |
| 2010/0076419 | A1 | * | 3/2010 | Chew ...................... A61F 9/008 606/6 |
| 2010/0249528 | A1 | | 9/2010 | Vayser et al. |
| 2012/0041268 | A1 | * | 2/2012 | Grey .................. A61B 1/00105 600/199 |
| 2012/0065556 | A1 | | 3/2012 | Smith et al. |
| 2012/0136216 | A1 | | 5/2012 | Vayser et al. |
| 2012/0265101 | A1 | * | 10/2012 | Korb et al. ................... 600/587 |
| 2013/0053733 | A1 | * | 2/2013 | Korb et al. ....................... 601/2 |
| 2013/0267786 | A1 | * | 10/2013 | Vayser .................... A61B 1/32 600/205 |
| 2014/0057223 | A1 | | 2/2014 | Vayser et al. |
| 2015/0005750 | A1 | * | 1/2015 | Kelleher et al. .................. 606/3 |
| 2015/0174425 | A1 | * | 6/2015 | Toyos ................... C12N 13/00 606/127 |
| 2015/0289936 | A1 | * | 10/2015 | Sotak .................. A61B 18/245 606/7 |
| 2015/0305938 | A1 | * | 10/2015 | Vold .................. A61B 19/5202 606/6 |
| 2016/0074126 | A1 | | 3/2016 | Vayser et al. |

OTHER PUBLICATIONS

European Patent Office; Communication Pursuant to Rules 702(2) and 70a(2) EPC, issued in connection to EP13856548.6; dated Aug. 11, 2016; 1 page; Europe.

European Patent Office; Communication and Extended European Search Report, issued in connection to EP13856548.6; dated Jul. 25, 2016; 6 pages.

* cited by examiner

Fig.9

EYELID TREATMENT DEVICE

RELATED APPLICATIONS

This application claims priority to provisional U.S. Patent Application No. 61/728,576, filed Nov. 20, 2012, which is incorporated by reference.

TECHNICAL FIELD

This technology relates to medical devices for applying electromagnetic treatment energy to an eyelid.

BACKGROUND

Meibomian glands produce secretions that contribute to the tear film of the eye. The meibomian glands are located within the eyelids, and have ducts with orifices at the margins of the eyelids. Obstructions to the flow of secretions outward through the ducts and orifices may cause a disorder known as meibomian gland dysfunction. This can be treated by the application of electromagnetic treatment energy, such as laser light, for heating an area of the eyelid to be treated.

SUMMARY OF THE INVENTION

A device includes an optical waveguide with a proximal input end for receiving electromagnetic treatment energy and a distal output end for emitting electromagnetic treatment energy. The device has an eyeball engagement surface with a concave contour, and has an oppositely facing eyelid engagement surface with a convex contour. The distal output end of the waveguide is located at the eyelid engagement surface.

In preferred embodiments, the device has a cylindrical proximal end portion including the proximal input end of the waveguide, and has a flattened distal end portion including the distal output end of the waveguide. The flattened distal end portion has a generally triangular, fan shaped peripheral configuration, and further has opposite side surface portions with arcuate contours for fitting between opposed arcuate surface portions of an eyeball and an eyelid.

Summarized differently, a device has a proximal end portion, a distal end portion, and an optical waveguide for transmitting electromagnetic treatment energy from the proximal end portion to the distal end portion. In a treatment position, the device reaches past a margin of an eyelid, and fits between an outer surface portion of an eyeball and an opposed inner surface portion of the eyelid. A first distal output end of the waveguide is oriented to emit and direct electromagnetic treatment energy to impinge upon the inner surface portion of the eyelid when the device is in the treatment position. A second distal output end of the waveguide is oriented to emit and direct electromagnetic treatment energy to impinge upon the margin of the eyelid when the device is in the treatment position.

DETAILED DESCRIPTION

The apparatus shown in the drawings has parts that are examples of the elements recited in the claims. The illustrated apparatus thus includes examples of how a person of ordinary skill in the art can make and use the claimed invention. It is described here to meet the enablement and best mode requirements of the patent statute without imposing limitations that are not recited in the claims.

Figure 1:
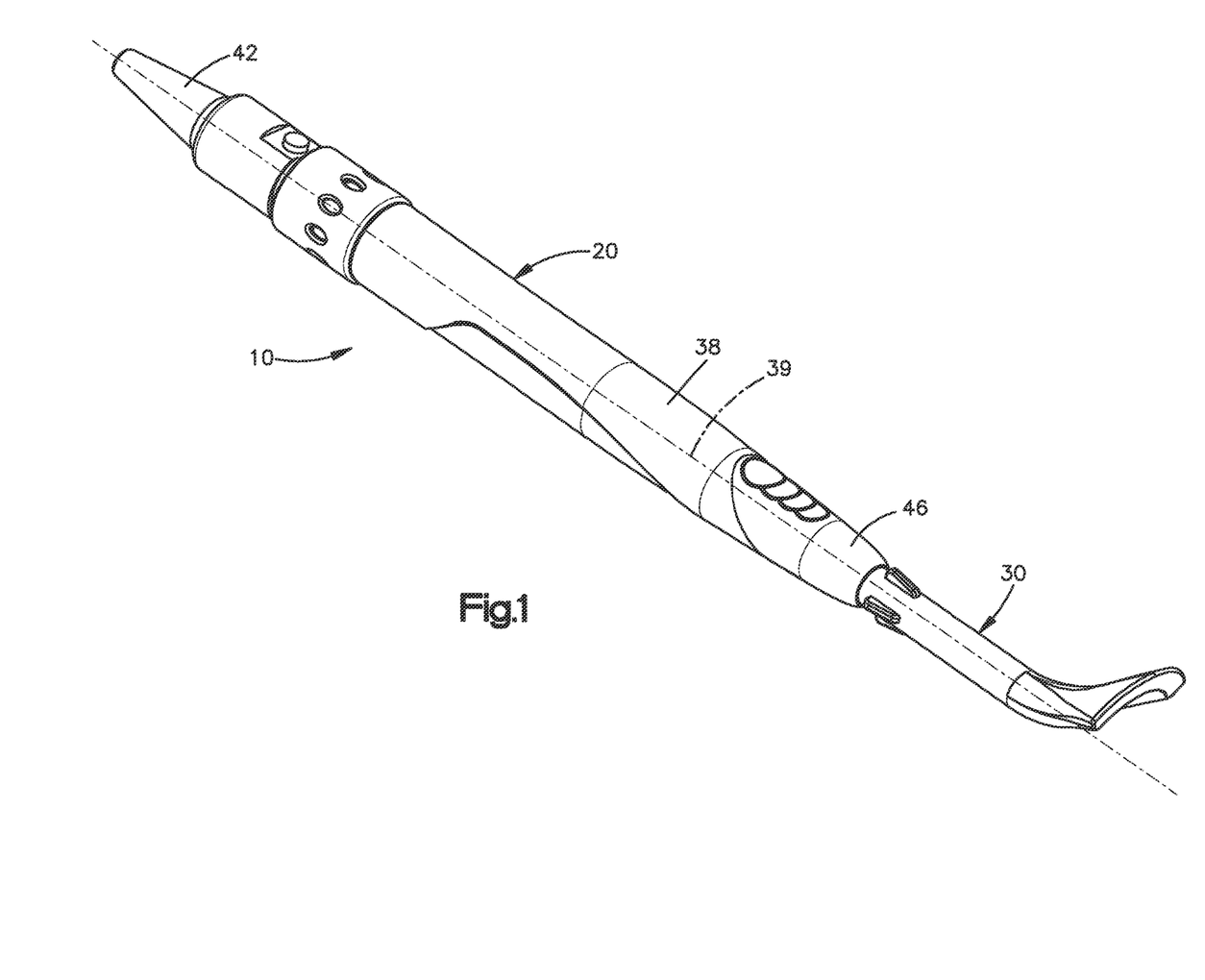
FIG. 1 is a perspective view of a handpiece with an eyelid treatment tip.

In the example shown in FIG. 1, an apparatus 10 includes a handpiece 20 with a tip 30. The handpiece 20 is configured to deliver electromagnetic treatment energy from a source to the tip 30. The tip 30 is configured to deliver the treatment energy to an eyelid. In the preferred embodiments, the treatment energy is laser light for treating meibomian gland dysfunction.

The handpiece 20 may comprise any suitable device known in the art. In the illustrated example, the handpiece 20 is a product of Biolase Inc. known by the trademark EZLase. A body portion 38 of the handpiece 20 is configured for manual use, and has an elongate, generally cylindrical configuration with a longitudinal central axis 39. A waveguide extends within the body 38 along the axis 39. A proximal end portion 42 of the body 38 is configured for detachably coupling the waveguide with a source of laser light. A distal end portion 46 of the body 38 is configured for detachably coupling the waveguide with the tip 30.

Figure 2:
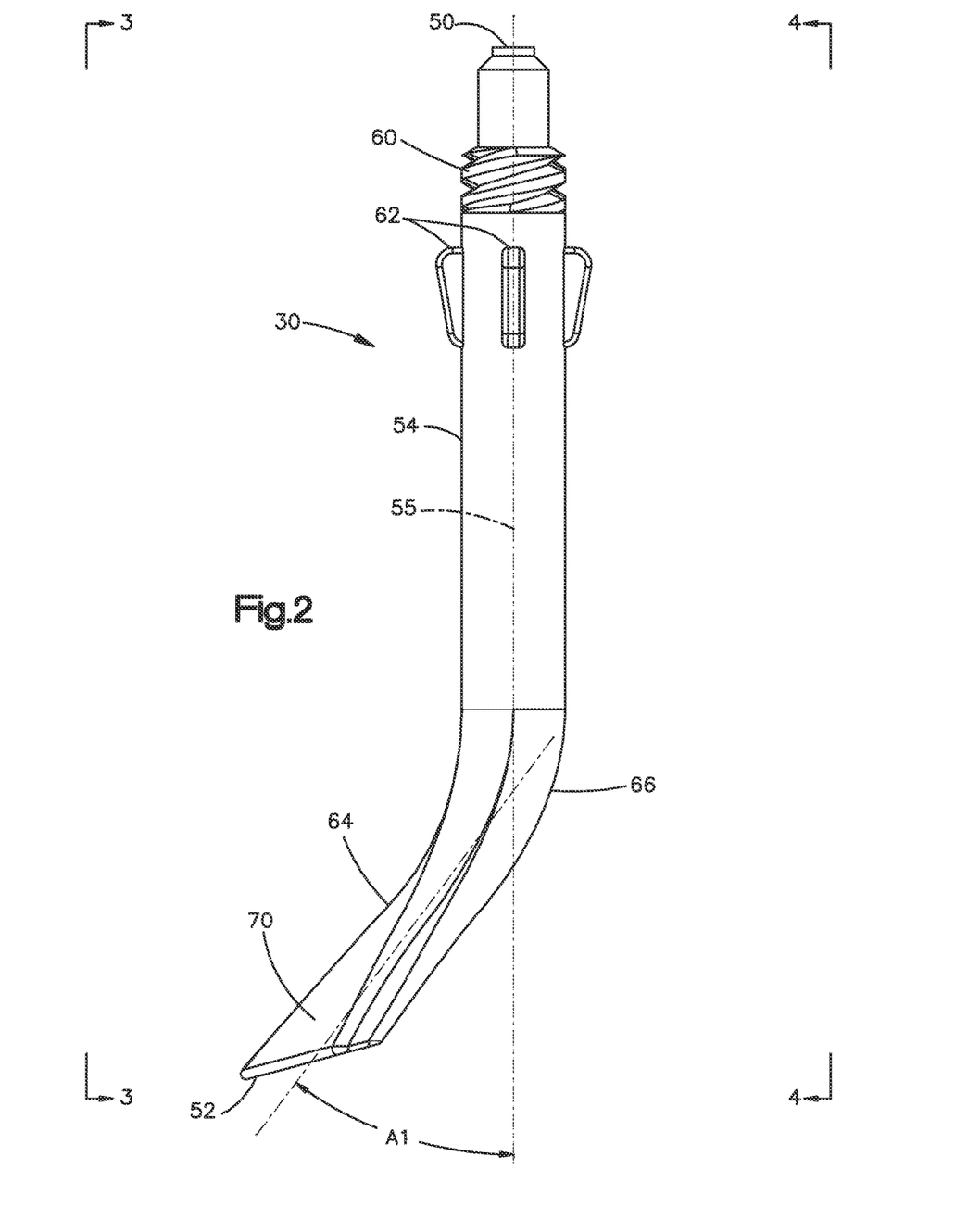
FIG. 2 is a side view of the tip shown in FIG. 1.
Figure 3:
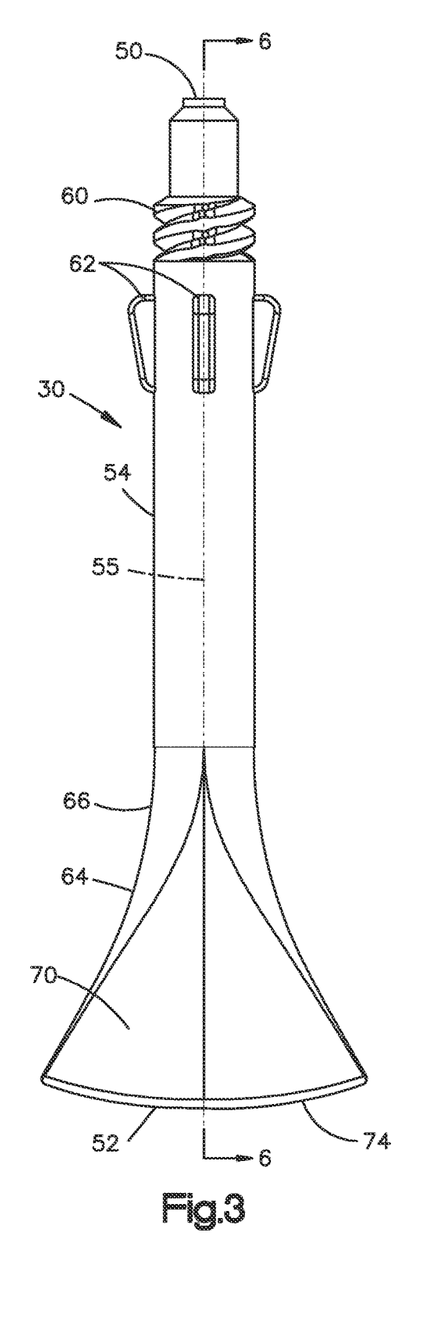
FIG. 3 is a top view taken on line 3-3 of FIG. 2.
Figure 4:
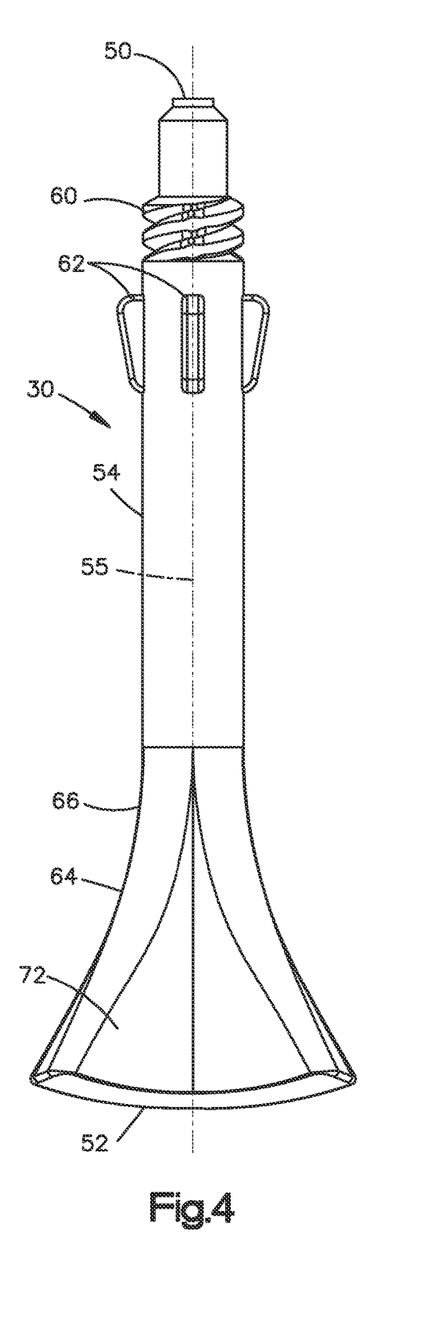
FIG. 4 is a bottom view taken on line 4-4 of FIG. 2.

As shown in FIGS. 2-4, this example of a tip 30 is an elongate device with terminal opposite ends 50 and 52. A proximal end portion 54 of the tip 30 has a cylindrical configuration with a longitudinal central axis 55. A coupling structure, which in the illustrated embodiment includes a screw thread 60 and manual rotation grips 62, is located on the proximal end portion 54 of the tip 30 for detachably coupling the tip 30 with the handpiece 20.

The tip 30 has a distal end portion 64, and further has a bend 66 at which the distal end portion 64 projects off the axis 55 of the proximal end portion 54. As viewed from the side in FIG. 2, the distal end portion 64 in the illustrated example projects off the axis 55 at an angle A1. The angle A1 may vary, but in the preferred embodiment is about 55 degrees.

The distal end portion 64 of the tip 30 is flattened relative to the cylindrical shape of the proximal end portion 54. The distal end portion 64 is also flared transversely outward from the cylindrical shape of the proximal end portion 54, as shown in FIGS. 3 and 4. This provides the distal end portion 64 with fan shaped, generally triangular upper and lower side surfaces 70 and 72.

Figure 5:
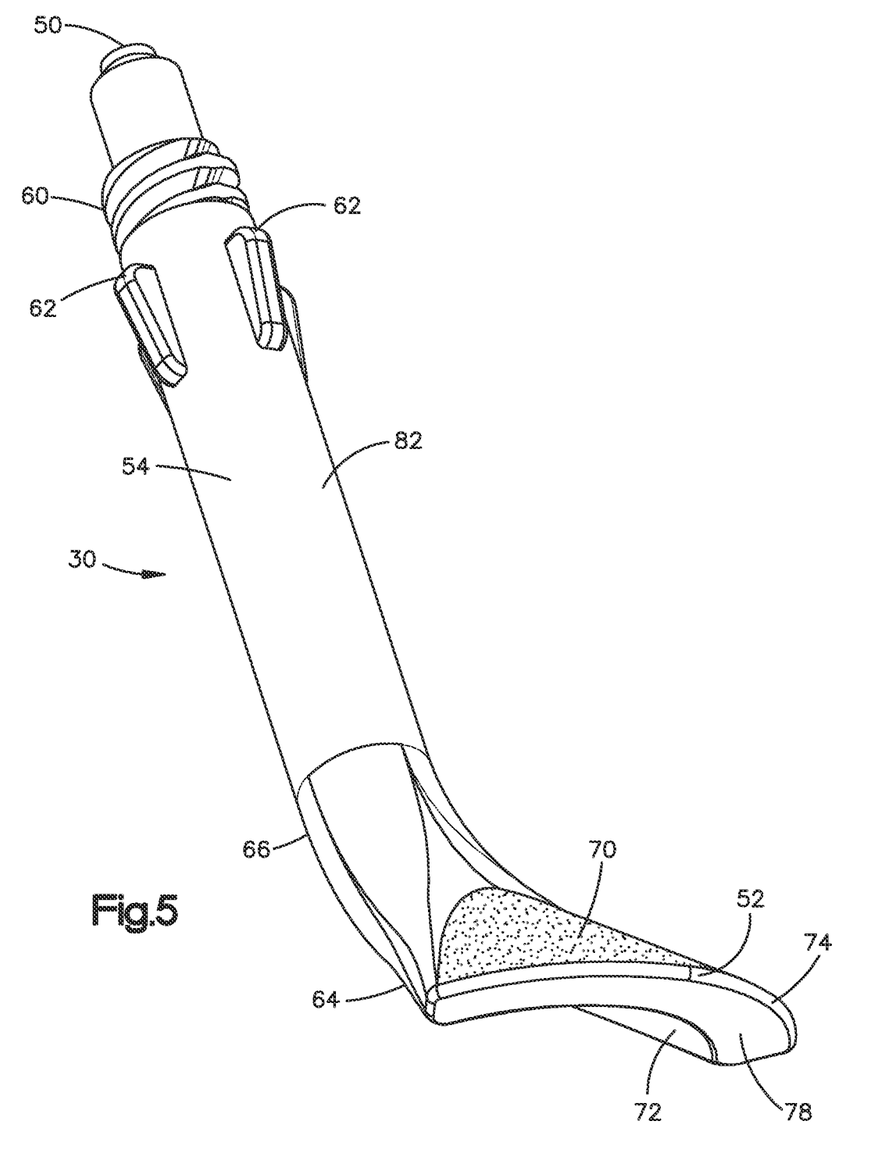
FIG. 5 is perspective view of the tip shown in FIGS. 1-4.

As shown in FIG. 5, the distal end portion 64 has an arcuate cross-sectional configuration. This provides the triangular upper side surface 70 with a convex contour, and provides the triangular lower side surface 72 with a concave contour. A rounded leading edge 74 defines the terminal distal end 52 of the tip 30 at the base of the triangular upper side surface 70.

A planar end surface 78 of the tip 30 has an arcuate peripheral shape with a width reaching radially between the upper and lower side surfaces 70 and 72. The end surface 78 is inclined to both the upper and lower side surfaces 70 and 72, as indicated by the angle A2 shown in FIG. 6, and reaches rearward from the leading edge 74 to the base of the lower side surface 72. The angle A2 also may vary, but in the preferred embodiment is about 45 degrees.

Figure 6:
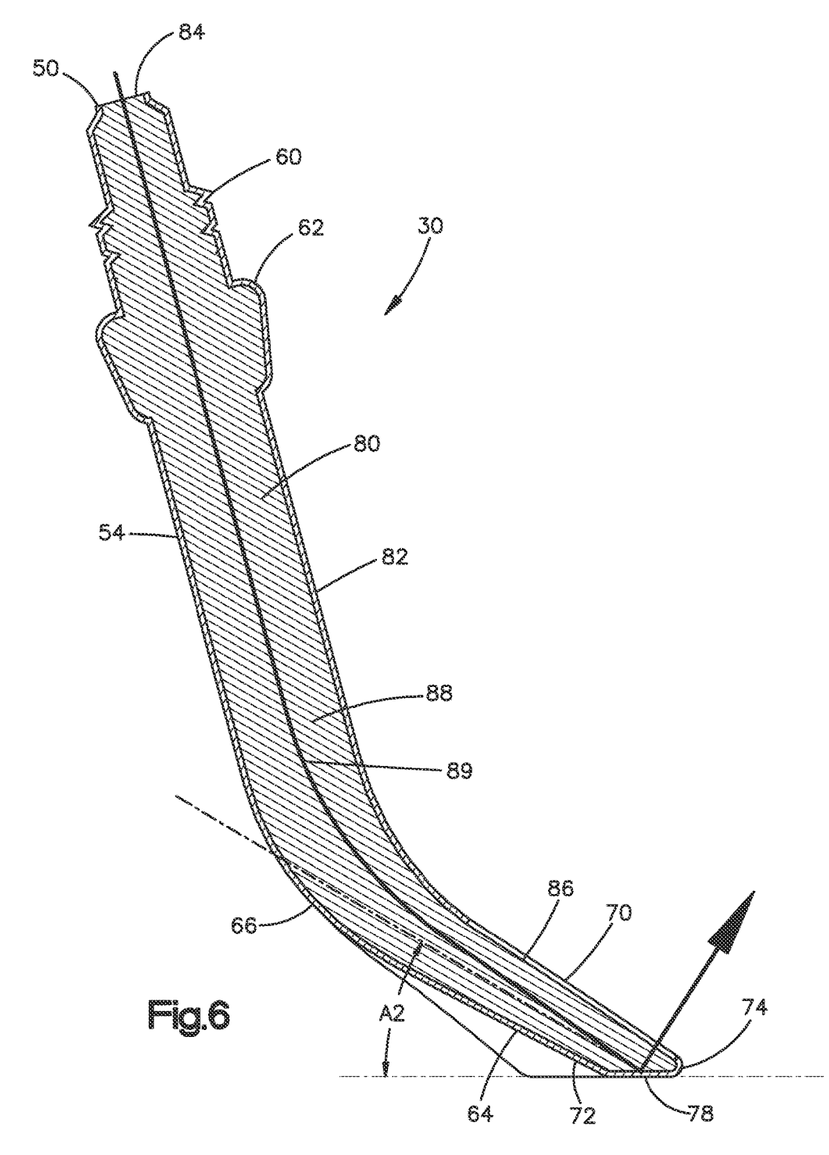
FIG. 6 is a sectional view taken on line 6-6 of FIG. 3.

As shown in FIG. 6, the tip 30 is preferably constructed as a unitary part consisting of a single continuous body 80 of light-transmitting material with an opaque reflective coating 82. The coating 82, which has an exaggerated thickness for illustration in the drawings, is discontinuous over a terminal proximal end surface 84 of the tip 30, and is also discontinuous over an area 86 at the upper side surface 70. The tip 30 is thus configured to provide a waveguide 88 having a proximal input end 84 for receiving electromagnetic treatment energy and a distal output end 86 for emitting electromagnetic treatment energy. As indicated by the example of a beam path 89 shown schematically in FIG. 6, the inclined planar end surface 78 is oriented for the coating 82 to reflect electromagnetic treatment energy toward and through the output end 86 of the waveguide 88 predominantly in a direction substantially perpendicular to the upper side surface 70.

Figure 7:
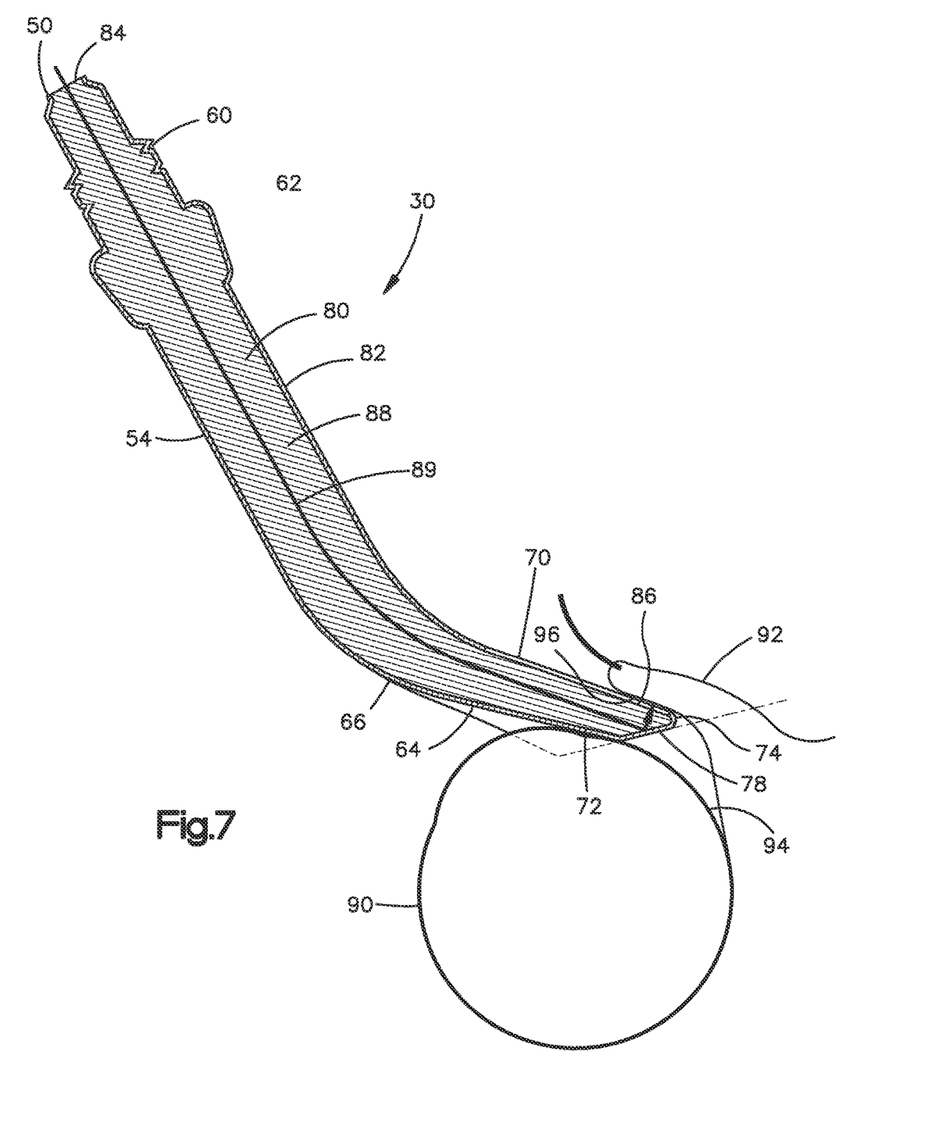
FIG. 7 is view similar to FIG. 5, showing the tip in a treatment position engaging an eyeball and an eyelid, which are shown schematically.

In use, the tip 30 is coupled with the handpiece 20 such that the proximal input end 84 of the waveguide 88 on the tip 30 is coupled with the distal output end of the waveguide on the handpiece 20. As shown in FIG. 7, the handpiece 20 is then manipulated to place the tip 30 in a treatment position inserted between an eyeball 90 and an eyelid 92. The angle A1 (FIG. 2) at the bend 66 assists the user with orienting the tip 30 in this manner. The rounded leading edge 74 of the tip 30, and the angle A2 (FIG. 6) at which the tip 30 is tapered to the leading edge 74, assist the user with lifting the eyelid 92 from the eyeball 90 for insertion and movement of the tip 30 toward the treatment position.

As the upper and lower side surfaces 70 and 72 of the tip 30 are advanced toward the position of FIG. 7, the upper side surface 70 serves as an eyelid engagement surface, and the lower side surface 72 serves as an eyeball engagement surface. Specifically, the contour of the lower side surface 72 corresponds to the spherical contour of the outer surface 94 of the eyeball 90. The contour of the upper side surface 70 likewise corresponds to the spherical contour of the adjacent inner surface 96 of the eyelid 92. This enables the tip 30 to adjoin and fit closely between those surfaces 94 and 96 with minimal discomfort for the patient. In this manner the distal output end 86 of the tip waveguide 88, which is located at the upper side surface 70, is positioned optimally for directing electromagnetic treatment energy to impinge upon the inner surface 96 of the eyelid 92. Such treatment energy may comprise, for example, laser light for heating the eyelid 92 to treat symptoms of meibomian gland dysfunction.

Figure 8:
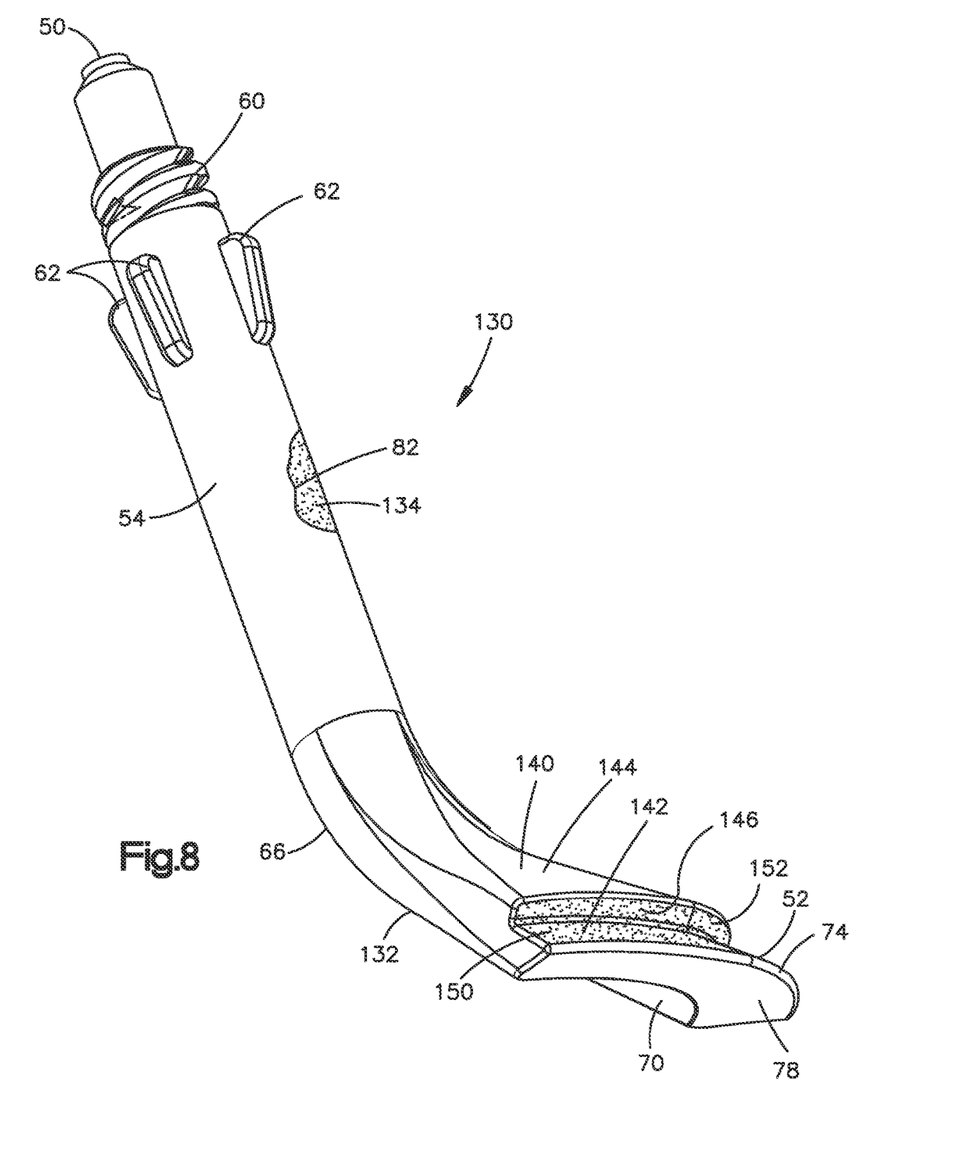
FIG. 8 is a perspective view of an alternative eyelid treatment tip.
Figure 9:
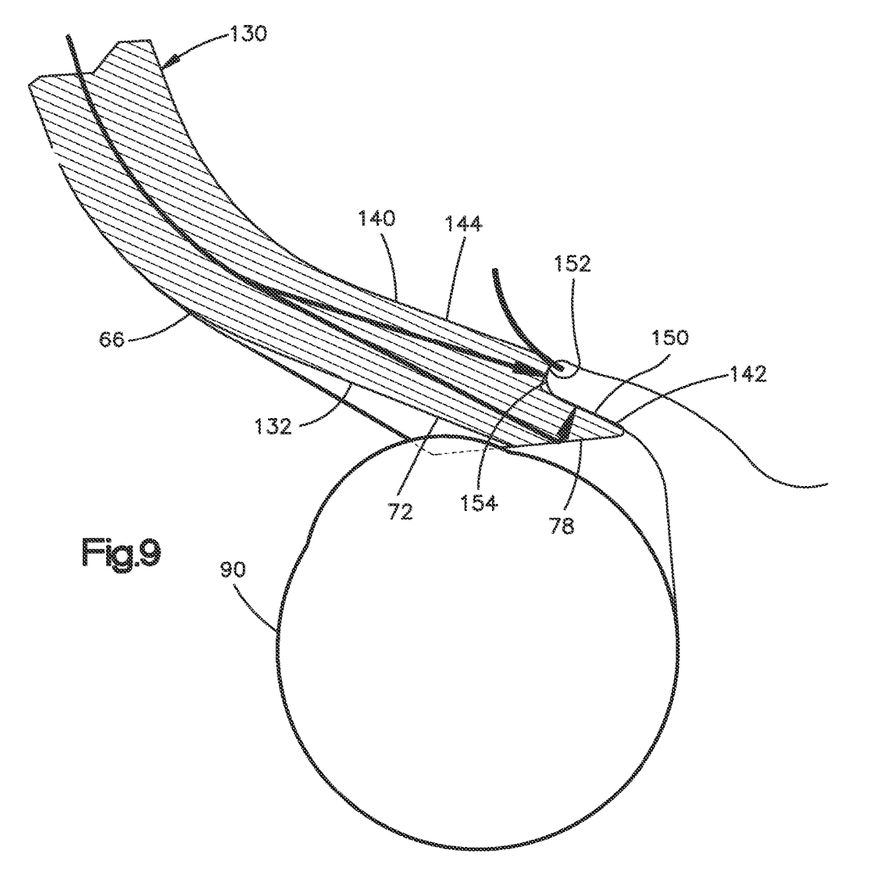
FIG. 9 is a view similar to FIG. 7, showing the tip of FIG. 8 in a treatment position.

An alternative tip 130 is shown in FIGS. 8 and 9. This tip 130 has many parts that are the same or substantially the same as corresponding parts of the tip 30 described above. Such parts are indicated by the use of the same reference numbers in the drawings of the two tips 30 and 130. The tip 130 of FIGS. 8 and 9 also has parts by which it differs from the tip 30, including a distal end portion 132 and a waveguide 134 that differ from the distal end portion 64 and the waveguide 88 at the tip 30.

The distal end portion 132 of the tip 130 has a generally triangular, convex upper side surface 140 with two distinct sections 142 and 144. A planar intermediate surface 146 has an arcuate peripheral shape with a width reaching radially between the two sections 142 and 144. In this configuration, the intermediate surface 146 defines a step up from the first section 142 to the second section 144.

The first section 142 of the upper side surface 140 is uncoated to provide the waveguide 134 with a first output end 150. The first output end 150 is oriented to emit electromagnetic treatment energy from the first section 142 of the upper side surface 140 predominantly in a direction substantially perpendicular to the first section 142. Additionally, the intermediate surface 146 is uncoated to provide the waveguide 134 with a second output end 152. The second output end 152 is oriented to emit electromagnetic treatment energy from the intermediate surface 146 predominantly in a direction reaching over and past the first section 142 of the upper side surface 140 substantially parallel to the first section 142. This enables the second output end 152 of the waveguide 134 to direct electromagnetic treatment energy to impinge upon meibomian gland orifices at the margin 154 of an eyelid when the tip 130 is in a treatment position, as shown for example in FIG. 9.

Figure 10:
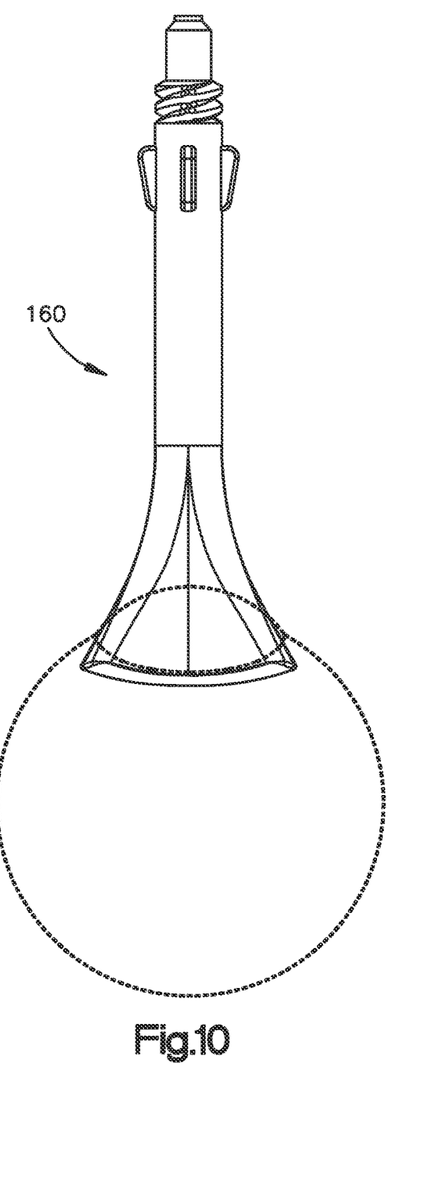
FIGS. 10 and 11 are views of additional alternative eyelid treatment tips.
Figure 11:
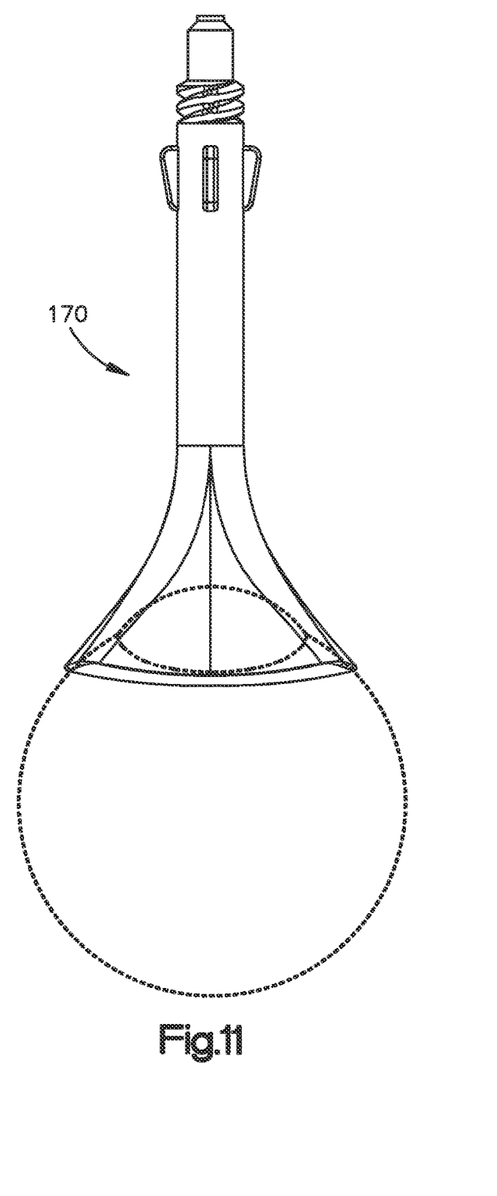

Other structural variations are illustrated in FIGS. 10 and 11, in which the arcuate reach of the leading edge of the tip is shown to differ between alternative embodiments 160 and 170 of the invention.

This written description sets forth the best mode of carrying out the invention, and describes the invention so as to enable a person skilled in the art to make and use the invention, by presenting examples of the elements recited in the claims. The patentable scope of the invention is defined by the claims, and may include other examples that occur to those skilled in the art. Such other examples, which may be available either before or after the application filing date, are intended to be within the scope of the claims if they have structural elements that do not differ from the literal language of the claims, or if they have equivalent structural elements with insubstantial difference from the literal language of the claims.

The invention claimed is:

1. An apparatus for a laser treatment of an eyelid of an eye, the apparatus comprising:
   a laser source configured to generate a laser beam for the laser treatment;
   an optical waveguide with a proximal input end for receiving the laser beam and a distal output end for emitting the laser beam,
   the waveguide including a proximal end portion including the proximal input end of the waveguide, a distal end portion including the distal output end of the waveguide,
   the distal end portion including a flattened flared arcuate tip sized and shaped to fit between an interior surface of the eyelid and an exterior surface of the eye, the tip includes an arcuate cross-section and two fan-shaped exterior sides opposite of each other, wherein the entire tip is at an angle from and projects asymmetrically off a central longitudinal axis of the proximal end portion, wherein the fan-shaped exterior sides comprise an eyeball engagement surface with a concave contour facing the longitudinal axis, and an eyelid engagement surface with a convex contour facing away from the longitudinal axis,
   wherein the tip is configured to guide the laser beam toward the eyelid and away from the eye, and includes a reflective surface at the distal output end that reflects the laser beam transversely to the eyelid engagement surface and toward the interior surface of the eyelid.

2. An apparatus as defined in claim 1, wherein the proximal end portion is cylindrical.

3. An apparatus as defined in claim 1, wherein the eyeball engagement surface and the eyelid engagement surface have triangular-shaped peripheral configurations.

4. An apparatus as defined in claim 1, wherein the waveguide has a rounded leading edge defining a terminal distal end of the waveguide, and the eyelid engagement surface has a triangular-shaped peripheral configuration with a base at the rounded leading edge.

5. An apparatus as defined in claim 4, wherein the eyeball engagement surface has a triangular-shaped peripheral configuration with a base that is spaced from the rounded leading edge in a direction toward the proximal input end of the waveguide.

6. An apparatus as defined in claim 1, wherein the waveguide has an elongated distal end surface with an arcuate peripheral configuration, elongated distal end surface extending between the eyeball engagement surface and the eyelid engagement surface.

7. An apparatus as defined in claim 1 wherein the distal output end of the waveguide is oriented to emit electromagnetic treatment energy in a first direction, and the waveguide has a second distal output end oriented to emit electromagnetic treatment energy in a second direction perpendicular to the first direction.

8. An apparatus as defined in claim 1, wherein the waveguide is a unitary part comprising a single, continuous body of light-transmitting material with an opaque reflective coating.

9. An apparatus as defined in claim 1, wherein the apparatus further comprises a handpiece, and wherein the waveguide is removable from the handpiece and serves as a handpiece tip.

10. An apparatus as defined in claim 9, wherein the distal output end of the waveguide is located at one of the side surface portions.

11. An apparatus as defined in claim 9, wherein the distal end portion of the handpiece tip has a rounded leading edge defining the terminal distal end of handpiece tip, and the triangular-shaped peripheral configuration has a base at the rounded leading edge.

12. An apparatus as defined in claim 9, wherein the handpiece tip is a unitary part comprising a single, continuous body of light-transmitting material with an opaque reflective coating.

* * * * *